United States Patent [19]

Watanabe et al.

[11] Patent Number: 4,751,221
[45] Date of Patent: Jun. 14, 1988

[54] 2-FLUORO-ARABINOFURANOSYL PURINE NUCLEOSIDES

[75] Inventors: Kyoichi A. Watanabe, Rye Brook, N.Y.; Chung K. Chu, Athens, Ga.; Jack J. Fox, White Plains, N.Y.

[73] Assignee: Sloan-Kettering Institute for Cancer Research, New York, N.Y.

[21] Appl. No.: 789,072

[22] Filed: Oct. 18, 1985

[51] Int. Cl.$^4$ .................. A61K 31/70; C07H 19/173
[52] U.S. Cl. ........................................ 514/46; 514/45; 536/24; 536/25
[58] Field of Search ............... 536/24, 25; 514/45, 514/46

[56] References Cited

U.S. PATENT DOCUMENTS 3,928,319 12/1975 Jenkins et al. .................. 536/26
4,145,531 3/1979 Eckstein et al. ................ 536/26

Primary Examiner—J. R. Brown
Assistant Examiner—Jenny Tou
Attorney, Agent, or Firm—John P. White

[57] ABSTRACT

2'-Deoxy-2'-fluoro-β-D-arabinofuranosyl nucleosides of the following structure are disclosed:

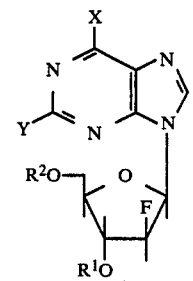

wherein

X and Y are the same or different and are hydrogen, $OR^3$, $SR^3$, $NR^3R^4$ or NHacyl wherein $R^3$ and $R^4$ are the same or different and are hydrogen, lower alkyl of 1 to 7 carbon atoms, aralky, or aryl;

NHacyl is alkanoyl or aroylamide;

$R^1$ and $R^2$ are the same or different and are hydrogen, acyl or aroyl.

6 Claims, No Drawings

2-FLUORO-ARABINOFURANOSYL PURINE NUCLEOSIDES

The invention described herein was made in the course of investigation under grants from the U.S. Department of Health and Human Services. The U.S. Government has certain rights in this invention.

BACKGROUND

This invention relates to novel purine nucleosides containing the 2'-deoxy-2'-fluoro-β-D-arabinofuranosyl moiety and potentially useful as antiparasitic agents, especially against Leishmania tropica.

The synthesis of 9-(2'-deoxy-2'-fluoro-β-D-arabinofuranosyl)adenine was reported from our laboratory as an analog of the antitumor and antiviral naturally-occurring nucleoside 9-(β-D-arabinofuranosyl)adenine (ara-A) [Wright et al., J. Org. Chem., 34, 2632 (1969)]. The synthesis consists of a multistep preparation of a 2-deoxy-2-fluoro-D-arabinofuranose derivative from D-xylose, and the 2-fluoro sugar is condensed with 2,6-dichloropurine by the fusion method, followed by multistep conversion of the purine into adenine.

Subsequently, 1-(2'-deoxy-2'-fluoro-β-D-arabinofuranosyl)cytosine (FAC) was synthesized in our laboratory by condensation of an appropriate sugar halide and cytosine by the silyl procedure, and FAC was evaluated for its antitumor activity [Wilson et al., J. Med. Chem., 13, 369 (1970)]. FAC was found to have a growth-inhibitory effect comparable with that of 1-(β-D-arabinofuranosyl)cytosine (ara-C) and 1-(β-D-arabinofuranosyl)-5-fluorocytosine (ara-FC) against L-1210 mouse leukemic cells in tissue culture.

We have since developed a more elegant and effective method for preparation of the 2-fluoro-arabinose from D-glucose [Reichman et al., Carbohyd. Res., 42, 233 (1975)] and prepared a number of 5-substituted-uracil and -cytosine nucleosides as potential antiviral and/or anticancer agents [Lopez et al., U.S. Pat. No. 4,171,429 (1979)]. Many pyrimidine nucleosides containing the 2'-fluoro-β-D-arabinofuranosyl moiety showed excellent antiherpesvirus activity [Fox et al., "Herpesvirus, Clinical, Pharmacological and Basic Aspects;" Shiota et al., eds; Excerpta Medica: Amsterdam, 1982; p.135] and some showed good antitumor activity [Burchenal et al., Cancer Res., 42, 2598 (1982)].

No purine nucleoside containing the 2'-fluoro-β-D-arabinofuranosyl moiety has been reported except the adenine nucleoside synthesized in our laboratory [Wright et al., loc. cit.], and no biological activity of the adenine nucleoside has been reported.

SUMMARY

Nucleosides of the invention can be represented by Formula I, as follows:

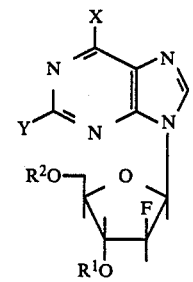

wherein
$X$ and $Y$ are the same or different and are hydrogen, $OR^3$ (keto or enol), $SR^3$, $NR^3R^4$, NH acyl or halogen such as chlorine or bromine;

$R^3$ and $R^4$ are the same or different and are hydrogen, lower alkyl of 1 to 7 carbon atoms such as methyl, ethyl, propyl and the like, aralkyl such as benzyl, benzhydryl, p-methoxybenzyl and the like, or aryl such as phenyl, p-chlorophenyl, toluyl, p-methoxyphenyl, naphtyl and the like.

NHacyl may be an alkanoyl or aroyl amide. The term "alkanoyl" is meant to include an alkyl carbonyl radical wherein alkyl is a straight or branched chain saturated or unsaturated hydrocarbon radical having from 1 to 20 carbon atoms.

$R^1$ and $R^2$ are the same or different hydrogen or acyl groups which may be alkanoyl group of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoleyl, oleyl, linolenyl, arachidonyl and the like. $R^1$ and $R^2$ can also be aroyl such as benzoyl and naphtoyl wherein the aromatic group may be additionally substituted by alkyl, alkoxy, halo or nitro moieties such as p-toluoyl, p-anisoyl, p-chlorobenzoyl, p-nitrobenzoyl or 2,4-dinitrobenzoyl and the like. $R^2$ may also be adamantoyl.

DESCRIPTION

The preferred starting materials for the process of the present invention can be subsumed under general Formula II as follows:

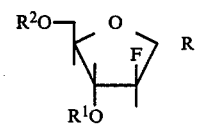

$R^1$ and $R^2$ are as defined previously.
$R$ is chlorine, bromine or acetoxy.

The synthesis of Formula II compounds has been reported by us (Reichman et al., loc. cit.).

The starting materials of Formula II are reacted with a nucleophile of general Formula III.

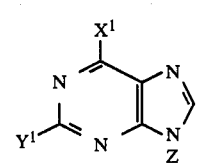

wherein $X^1$ and $Y^1$ are the same or different and are hydrogen, $OR^5$ (keto or enol), $SR^5$, $NR^5R^6$, halogen such as chlorine or bromine or silylated Nacyl;

$R^5$ and $R^6$ are the same or different and are hydrogen, tri-substituted-silyl, lower alkyl of 1 to 7 carbon atoms such as methyl, ethyl, propyl and the like, aralkyl such as benzyl, benzhydryl, p-methoxybenzyl and the like, or aryl such as phenyl, p-chlorophenyl, toluyl, p-methoxyphenyl, naphtyl and the like.

Silylated N aryl is an alkanoyl or aroyl amide in which the dissociable amide proton is substituted by a tri-substituted-silyl group.

Tri-substituted-silyl may be trimethyl-, triethyl-, tripropyl-, tri-isopropyl-, tributyl-, tert-butyldimethyltetramethylene-isopropyl-, tetramethylene-tert-butyl-, tribenzyl-, or phenyldimethyl- or the like.

Z is hydrogen, tri-substituted-silyl or heavy metal derivative such as chloromercuri, bromomercuri, acetoxymercuri or the like.

The reaction is carried out in an appropriate solvent such as halogenated hydrocarbon (e.g., methylene chloride, chloroform, 1,2-dichloroethane, etc.), aromatic hydrocarbon (benzene, toluene, xylene, etc.), carboxylic acid derivatives such as ethyl acetate, acetonitrile or N,N-dimethylformamide with or without drying agents (e.g., Drierite or molecular sieves) at a temperature range of from 25° C. to 200° C. in a period of from one hour to ten days.

The molar ratio of the reactants, Formula II to Formula III, can be 1:10, preferably 1:3.

Upon completion of the reaction, the mixture is filtered and the filtrate condensed in vacuo. When a heavy metal derivative is used, the residue is redissolved in halogenated hydrocarbon solvent (preferably chloroform) and the solution washed successively with 30% potassium iodide solution and water, dried over sodium sulfate, magnesium sulfate or calcium chloride and re-evaporated to dryness in vacuo.

3′,5′-Di-O-acyl nucleosides (Formula I) can be obtained in pure condition either by direct cyrstallization of the residue from various solvents such as alkanol preferably ethanol or methanol, or solvent systems such as alkanol-dialkyl ether or petroleum ether, preferably ethanol-diethyl ether, or by chromatography over a column of silica gel using various solvent systems preferably chloroform-methanol (40:1 v/v) as the eluent.

The free nucleoside of Formula I wherein $R^1$ and $R^2$ are hydrogen, is obtained by either saponification of the 3′,5′-di-O-acyl intermediate with alkali metal alkoxide in alkanoyl preferably 0.01 to 0.1M sodium methoxide in methanol, or when X is not SH, SR or halogen by treatment of the 3′,5′-protected nucleoside with amine-alkanol mixture preferably 10% to 30% methanolic ammonia at a temperature between −10° C. and 100° C., preferably 10° C. to 30° C. for five minutes to three days.

The free nucleoside of Formula I wherein X is halogen (Cl or Br) and $R^1$ and $R^2$ hydrogen, is prepared from the corresponding 3′,5′-di-O-alkanoyl intermediate (Formula I wherein X is Cl or Br and $R^1$ and $R^2$ are the same or different lower alkanoyl groups such as acetyl, propionyl, butyryl and the like) by treatment with mineral acid water or alkanoyl preferably 5% to 15% hydrogen chloride in methanol.

Formula I 6-thiopurine nucleosides wherein X is SH are obtained by thiation of a Formula I 3′,5′-di-O-acyl nucleosides wherein X is OH with phosphorus pentasulfide ($P_2S_5$) or Lawsson's reagent [2,4-bis(4-methoxyphenyl)-1,3-dithia-2,4-diphosphetane-2,4-disulfide] in dioxane or in pyridine at reflux temperature for a period of ten minutes to 24 hours. The molar ratio with respect to the thiating reagent is from 1:0.5 to 1:1. The free 6-thiopurine nucleosides are obtained by saponification as described previously. The 6-thiopurine nucleosides can also be obtained from the corresponding 6-halopurine nucleosides by treatment with thiourea to form the corresponding thiuronium salts followed by acid hydrolysis. The 2-thiopurine nucleosides of Formula I (Y is SH) can be obtained from the corresponding 2-halopurine nucleosides by treatment with thiourea followed by acid hydrolysis of the intermedial (intermediate?) thiuronium salts.

6-Alkylmercapto- or 6-aralkylmercaptopurine nucleosides wherein X is SR, is obtained by treatment of the free 6-thiopurine nucleosides (Formula I, X=SH, $R^1$=$R^2$=H) with alkyl or aralkyl halide or dialkyl sulfate in water or alkanol in the presence of alkali metal hydroxide or carbonate or alkalimetal alkoxide, preferably 1.0 to 1.2 equivalents of sodium hydroxide in water or 1.0 to 1.2 equivalents of sodium methoxide in methanol. Alkyl halide designates bromide or iodide of lower alkyl of 1 to 5 carbon atoms such as methyl, ethyl, propyl, isopropyl, tert-butyl, pentyl and the like. Aralkyl halide includes chloride or bromide of benzyl, p-chlorobenzyl, p-methylbenzyl, p-methoxybenzyl, p-nitrobenzyl, o-nitrobenzyl and the like.

6-Amino-substituted nucleosides (Formula I, $R^1,R^2$=H, X=$NR^3R^4$ wherein $R^3$ and $R^4$ may be the same or different groups such as H, alkyl, aralkyl or aryl as defined previously) are also obtained from 6-thio nucleosides (Formula I, X=SH, $R^1,R^2$=H), 6-alkyl- or aralkylmercapto nucleosides (Formula I, X=SR, $R^1,R^2$=H), 6-halo nucleosides (Formula I, X=Cl or Br, $R^1,R^2$=H) or their 3′,5′-di-O- and analogs (Formula I, X=SH, SR, Cl or Br and $R^1$ and $R^2$ are the same or different alkanoyl or aroyl groups) by treatment with the corresponding amine (including ammonia) in water or alkanol (preferably methanol) at a temperature range of 0° C. to 160° C., under a pressure range from 1 to 5 atoms.

6-Hydroxy-substituted nucleosides (Formula I wherein X is OH) are prepared by acid hydrolysis of 6-amino-, 6-thio- or 6-substituted-thio nucleosides (Formula I, X=$NR^3R^4$, SH or SR), or by base hydrolysis of 6-halo- nucleosides (Formula I, X=Cl or Br).

5′-O-Alkanoyl nucleosides (Formula I, $R^2$=alkanoyl group of 4 to 20 carbon atoms, $R^1$, X and Y are defined for Formula I) are obtained by treatment of the corresponding free nucleoside or the HCl salt (if the nucleoside contains amino group) with 1.1 equivalents of alkanoyl halide in N,N-dimethyl formamide or N,N-dimethyl acetamide at a temperature range of 0° C. to 100° C. preferably at room temperature for a period of one to 72 hours. Alkanoyl halide includes chloride or bromide of saturated or unsaturated fatty acid containing 4 to 20 carbon atoms such as n-butyric, isobutyric, n-valeric, isovaleric, caproic, capric, lauric, myristic, palmitric, stearic, aractidic, stilligic, palmitoleic, oleic, linolenic or arachidonic acid and the like.

After completion of the reaction, the mixture is concentrated in vacuo and the residue is thoroughly triturated first with ether, preferably diethyl ether, and then by 1–2N sodium bicarbonate solution. The residue is crystallized from an appropriate alkanol such as methanol, ethanol, propanol and the like from an alkanoic acid ester such as ethyl acetate, methyl propionate and the like or a mixture of such solvents.

5'-O-Aroyl nucleosides (Formula I, $R^2$=aroyl such as benzoyl, toluoyl, p-chlorobenzoyl, p-nitrobenzoyl, anisoyl, naphtoyl, and the like; $R^1$=H; X and Y are as defined for Formula I) and 5'-O-adamantoyl nucleoside (Formula I, $R^2$=adamantoyl; $R^1$=H; X and Y are as defined for Formula I) are also prepared by a similar manner from the corresponding free nucleosides or the HCl salt (if the nucleoside contains amino group) by treatment with 1.5 to 4 equivalents of the corresponding acid halides.

The free nucleoside (Formula I wherein X and/or Y are amino, monosubstituted amino, or disubstituted amino group(s)) forms acid addition salts with both organic and inorganic acids. Preferably, acid addition salts are the pharmaceutically acceptable acid addition. Non-pharmaceutically acceptable (Pharmaceutically unacceptable?) acid addition salts can be converted to the pharmaceutically (pharmacologically?) acceptable acid addition salts by ion-exchange techniques, well known in the art. Examples of pharmaceutically acceptable acid addition salts include hydrochloric acid, hydrobromic acid, sulfuric acid, phosphoric acid, citric acid, tartaric acid, acetic acid, gluconic acid and the like.

The free nucleosides (Formula I) and their acid addition salts are useful therapeutic agents exhibiting antiparasitic and/or anticancer activity. They may be employed in the form of pharmaceutical preparations which contain them in association with a comparable pharmaceutical carrier, which can be an organic or inorganic inert carrier material, suitable for enteral or parenteral administration. Examples of such carrier material would include water, gelatin, gum arabic, lactose, starches, magnesium stearate, talc, vegetable oils, polyalkylene glycols, petroleum jelly, etc. The pharmaceutical preparations can be made up in solid form (e.g., as tablets dragees or capsules) or in liquid form (e.g., as solutions, suspensions or emulsions). The preparations may be sterilized and/or may contain adjuvants such as preserving, stablizing, wetting or emulsifying agents, salts for varying the osmotic pressure or buffers. Such preparations may also contain other therapeutic agents.

The following are intended to further illustrate the inventions without limiting same.

EXAMPLE 1

A mixture of 3-O-acetyl-benzoyl-2-deoxy-2-fluoro-D-arabinofuranosyl bromide (903 mg, 2.5 mmol), $N^6$-benzoyladenine (1.48 g, 6.2 mmol) and molecular sieves (4 A, 3 g) in methylene chloride (25 ml) is refluxed for three days with vigorous stirring. After cooling to room temperature, the mixture is filtered through a Celite pad. The filtrate which contains two major products (Rf=0.08 and 0.99 on a silica gel thin-layer plate, 9:1 methylene chloride-methanol) is concentrated in vacuo, and the residue is chromatographed over a silica gel column using 20:1 methylene chloride-methanol and 9-(3'-O-acetyl-5'-O-benzoyl-2'-deoxy-2'-fluoro-β-D-arabinofuranosyl)-$N^6$-benzoyl adenine (440 mg, 34%) is obtained as a foam from the slower moving major fraction.

Anal. Calcd for $C_{26}H_{22}FN_5O_6$: C, 60.12; H, 4.24; F, 3.66; N, 13.49. Found: C, 59.23: H, 4.46: F, 3.66: N, 13.13.

By following the same procedure but using the corresponding purine analogs as starting materials, the following compounds are also prepared:

9-(3'-O-acetyl-5'-O-benzoyl-2'-deoxy-2'-fluoro-β-D-arabinofuranosyl)-$N^6$-acetyladenine.

9-(3'-O-acetyl-5'-O-benzoyl-2'-deoxy-2'-fluoro-β-D-arabinofuranosyl)-$N^6$-benzoyl-2-chloroadenine.

9-(3'-O-acetyl-5'-O-benzoyl-2'-deoxy-2'-fluoro-β-D-arabinofuranosyl)-$N^6$-acetyl-2-chloroadenine.

9-(3'-O-acetyl-5'-O-benzoyl-2'-deoxy-2'-fluoro-β-D-arabinofuranosyl)-$N^6$-benzoyl-2-bromoadenine.

9-(3'-O-acetyl-5'-O-benzoyl-2'-deoxy-2'-fluoro-β-D-arabinofuranosyl)-$N^6$-acetyl-2-bromoadenine.

EXAMPLE 2

A mixture of mercury salt of 2-acetamide-6-chloropurine (8.8 g, 20 mmol) [Acton and Iwamato, Synth Proc. Nucleic Acid Chem., 1, 25 (1968)] and Celite (4.0 g) in xylene (400 ml) is dried by distilling off~200 ml of xylene. The suspension is cooled to room temperature and to it is added a solution of 3-O-acetyl-5-O-benzoyl-2-deoxy-2-fluoro-D-arabinofuranosyl bromide (7.2 g, 20 mmol) in xylene (80 ml). The mixture is heated with stirring for 15 hours at reflux temperature and filtered hot. The filtrate is concentrated in vacuo and the residue dissolved in chloroform (200 ml). The solution is washed successively with 30% potassium iodide solution (80 ml×2 ) and water (100 ml×2), dried, evaporated, and the residue chromatographed on a silica gel column using 30:1 chloroform-methanol as the eluent. The major nucleoside fraction is concentrated in vacuo and the residue is crystallized twice from ethanol to afford 9-(3'-O-acetyl-5'-O-benzoyl-2'-deoxy-2'-fluoro-β-D-arabinofuranosyl)-2-acetamido-6-chloropurine (1.65 g, 17%), mp 154°–156° C.

Anal. Calc for $C_{20}H_{19}ClFN_5O_6$: C, 51.27; H, 3.87; Cl, 7.22; F, 3.87; N, 14.24. Found: C, 51,12; H, 4.15; Cl, 7.33; F, 3.87; N, 14.67.

By following the same procedure but using mercury salt of corresponding purine analogs as starting materials, the following compounds are also prepared:

9-(3'-O-acetyl-5'-O-benzoyl-2'-deoxy-2'-fluoro-β-D-arabinofuranosyl)-2-acetamidopurine.

9-(3'-O-acetyl-5'-O-benzoyl-2'-deoxy-2'-fluoro-β-D-arabinofuranosyl)-2-acetamido-6-bromopurine.

9-(3'-O-acetyl-5'-O-benzoyl-2'-deoxy-2'-fluoro-β-D-arabinofuranosyl)-6-chloropurine.

9-(3'-O-acetyl-5'-O-benzoyl-2'-deoxy-2'-fluoro-β-D-arabinofuranosyl)-6-bromopurine.

EXAMPLE 3

A mixture of 9-(3'-O-acetyl-5'-O-benzoyl-2'-deoxy-2'fluoro-β-D-arabinofuranosyl)-2-acetamido-6-chloropurine (1.5 g, 3.05 mmol) and thiourea (1.5 g, 20 mmol) in ethanol (20 ml) is heated at reflux for 18 hours. After cooling, the mixture is filtered, the filtrate concentrated in vacuo, and the residue chromatographed on a silica gel column using 30:1 chloroform-methanol as the eluent. The major nucleoside-containing fractions are collected, evaporated in vacuo, and the residue crystallized from ethanol to give 9-(3'-O-acetyl-5'-O-benzoyl-2'-deoxy-2'-fluoro-β-D-arabinofuranosyl)-2-acetamido-6-thiopurine (250 mg), mp 136°–139° C.

Anal. Calcd for $C_{21}H_{20}FN_5O_6S$: C, 51.53; H, 4.09; F, 3.89; N, 14.31; S, 6.54. Found: C, 51.34; H, 4.31; F, 3.97; N, 14.94; S, 6.55

By following the same procedure but using the corresponding 6-chloropurine nucleosides as starting materials, the following 6-thiopurine nucleosides are prepared:
9-(3'-O-acetyl-5'-O-benzoyl-2'-deoxy-2'-fluoro-β-D-arabinofuranosyl)-6-thiopurine.
9-(3'-O-acetyl-5'-O-benzoyl-2'-deoxy-2'-fluoro-β-D-arabinofuranosyl)-2-methoxy-6-thiopurine.
9-(3'-O-acetamido-5'-O-benzoyl-2'-deoxy-2'-fluoro-β-D-arabinofuranosyl)-2-benzamido-6-thiopurine.

EXAMPLE 4

9-(3'-O-Acetyl-5'-O-benzoyl-2'-deoxy-2'-fluoro-β-D-arabinofuranosyl)-2-acetamido-6-thiopurine (190 mg, 0.39 mmol) is dissolved in 1M-methanolic sodium methoxide (6.5 ml) and the mixture is heating at reflux temperature for three hours. After cooling to room temperature, the mixture is neutralized with Dowex 50 (H+), filtered, and the filtrate concentrated in vacuo. 9-(2'-deoxy-2'-fluoro-β-D-arabinofuranosyl)-2-amino-6-thiopurine is obtained as colorless crystals upon trituration of the residue with ethanol, (74 mg), mp 244°–245° C. (dec).

Anal. Calcd for $C_{10}H_{12}FN_5O_3S$: C, 39.87; H, 3.99; F, 6.31; N, 23.26; S, 10.63. Found: C, 39.75; H, 4.07; F, 6.14; N, 23.16; S, 10.41.

By following the same procedure but using the corresponding protected nucleosides as starting materials, the following nucleosides are prepared:
9-(2'-deoxy-2'-fluoro-β-D-arabinofuranosyl)-2,4-diaminopurine.
9-(2'-deoxy-2'-fluoro-β-D-arabinofuranosyl)-2-aminopurine.
9-(2'-deoxy-2'-fluoro-β-D-arabinofuranosyl)-guanine.
9-(2'-deoxy-2'-fluoro-β-D-arabinofuranosyl)-6-thiopurine.
9-(2'-deoxy-2'-fluoro-β-D-arabinofuranosyl)-6-methoxypurine.
9-(2'-deoxy-2'-fluoro-β-D-arabinofuranosyl)-2-methoxy-6-thiopurine.

EXAMPLE 5

To a solution of 9-(2'-deoxy-2'-fluoro-β-D-arabinofuranosyl)adenine (140 mg, 0.52 mmol) in 50% aqueous acetic acid (8 ml) is added sodium nitrite (100 g in four portions at every 12 hours, and the reaction is followed by thin layer chromatography on silica gel plates (13:4:1 ethylacetateisopropanol-water). After all the starting material is consumed, the mixture is passed through a Dowex 50 (H+) column (5×0.5 cm). The column is washed with water. The major nucleoside-containing fractions are collected and lyophilized to afford 9-(2'-deoxy-2'-fluoro-β-D-arabinofuranosyl)-hypoxanthin (35 mg) as a colorless fluffy solid.

Anal. Calcd for $C_{10}H_{11}FN_4O_4 \cdot H_2O$: C, 41.67; H, 4.51; F, 6.60; N, 19.44. Found: C, 41.84; H, 4.22; F, 6.76; N, 19.81.

By following the same procedure but using the corresponding adenine nucleosides, the following compounds are also prepared:
9-(2'-deoxy-2'-fluoro-β-D-arabinofuranosyl)-2-chlorohypoxanthine
9-(2'-deoxy-2'-fluoro-β-D-arabinofuranosyl)-2-methoxyhypoxanthine
9-(2'-deoxy-2'-fluoro-β-D-arabinofuranosyl)-2-methylthiohypoxanthine

EXAMPLE 6

A mixture of 9-(2'-deoxy-2'-fluoro-β-D-arabinofuranosyl)-6-thiopurine (136 mg, 0.48 mmol) and methyl iodide (141 mg, 1.0 mmol) in 0.2N sodium hydroxide (2.5 ml) is stirred at room temperature for 2 hours. After concentration of the mixture in vacuo, the residue is triturated with acetone (2 ml). 9-(2'-deoxy-2'-fluoro-β-D-arabinofuranosyl)-6-methylthiopurine is obtained in its pure state by recrystallization of the acetone insoluble solid from ethanol (0.67 mg), mp 152°–153° C.

Anal. Calcd for $C_{11}H_{13}FN_4O_3S$: C, 44.00; H, 4.33; F, 6.33; N, 18.67; S, 10.67. Found: C, 43.94; H, 4.40; F, 6.53; N, 18.52; S, 10.80.

By following the same procedure but using the corresponding 6-thiopurine nucleosides, the following 6-methylthioderivatives aer also prepared:
9-(2'-deoxy-2'-fluoro-β-D-arabinofuranosyl)-2-amino-6-methylthiopurine
9-(2'-deoxy-2'-fluoro-β-D-arabinofuranosyl)-2-methoxy-6-methylthiopurine

EXAMPLE 7

A mixture of 9-(3'-O-acetyl-5'-O-benzoyl-2'-deoxy-2'-fluoro-β-D-arabinofuranosyl)-2-acetaamido-6-chloropurine (600 mg, 1.22 mmol), 2-mercaptoethanol (0.6 ml) and 0.375M sodium methoxide in methanol (16 ml) is gently refluxed for 15 hours. The mixture is cooled to 0° C. and crystalline precipitates are collected by filtration, dissolved in water (10 ml), neutralized with Dowex 50 (H+). After removal of the resin by filtration, the filtrate is concentrated in vacuo and the residue is recrystallized from water to give 9-(2'-deoxy-2'-fluoro-β-D-arabinofuranosyl)-guanine (73 mg), mp 250°–251° C.

Anal. Calcd for $C_{10}H_{12}FN_5O_4 \cdot \frac{1}{2}H_2O$: C, 40.82; H, 4.42; F, 6.46; N, 23.81. Found: C, 41.04; H, 4.35; F, 6.59; N, 23.71.

In a similar manner, 9-(2'-deoxy-2'-fluoro-β-D-arabinofuranosyl)hypoxanthine is prepared from 9-(3'-O-acetyl-5'-O-benzoyl-2'-deoxy-2'-fluoro-β-D-arabinofuranosyl)-6-chloropurine.

EXAMPLE 8

A mixture of 9-(2'-deoxy-2'-fluoro-β-D-arabinofuranosyl)-6-thiopurine (140 mg, 0.49 mmol) and Raney nickel (100 mg) in water (5 ml) is heated at reflux for two hours and the mixture is filtered, while hot, through a Celite pad. The filtrate is concentrated in vacuo and the solid residue is recrystallized from methanol to give 9-(2'-deoxy-2'-fluoro-β-D-arabinofuranosyl)-purine (66 mg), mp 173°–175° C.

Anal. Calcd for $C_{10}H_{11}FN_4O_3$: C, 47.24; H, 4.33; F, 7.48; N, 22.05. Found: C, 47.22; H, 4.33; F, 7.68; N, 22.05.

By following the same procedure but using the corresponding 6-thiopurine nucleosides, the following compounds are also prepared:
9-(2'-deoxy-2'-fluoro-β-D-arabinofuranosyl)-2-aminopurine.
9-(2'-deoxy-2'-fluoro-β-D-arabinofuranosyl)-2-methoxypurine.

BIOLOGICAL ACTIVITIES

Compounds of the invention show antitumor and antitripanosomal activities. Table 1 lists antitumor activity of representative nucleosides. 9-(2'-deoxy-2'- fluoro-β-D-arabinofuranosyl)guanine and 9-(2'-deoxy-2'-fluoro-β-D-arabinofuranosyl)-6-thioguanine exhibit potent inhibitory activity against human tumor cell lines, Namalva and CCRF-CEM, although their activity against mouse leukemic cells L-1210 and P-815 is modest.

TABLE 1

Cytotoxicity of 9-(2'-Deoxy-2'-fluoro-β-D-arabinofuranosyl)purines.

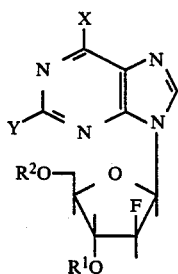

| X | Y | L-1210[a] | P-813[a] | NL[b] | CCRF—CEM[b] |
|---|---|---|---|---|---|
| OH | H | >30 | >30 | ~30 | 15.1 |
| OH | NH₂ | 2.0 | 5.4 | 0.7 | <0.10 |
| SH | NH₂ | 11.0 | 4.6 | 1.2 | 0.10 |
| SH | H | 27.0 | 10.0 | 2.0 | 10.0 |
| NH₂ | H | >30 | >30 | 3.0 | 0.67 |

ID$_{50}$ (μM)

[a]Mouse leukemia cells
[b]Human cells 9-(2'-Deoxy-2'-fluoro-β-D-arabinofuranosyl)hypoxanthine inhibits the growth of *Leishmania tropica* promastigotes by 50% at the concentration of 0.6 μM, while it does not exhibit any cytotoxicity against L-1210 cells at the concentration of 100 μM.

What is claimed is:

1. A purine nucleoside having the structural formula:

wherein X and Y are the same or different and are hydrogen, halogen, OR$^3$, SR$^3$, NR$^3$R$^4$ or NHacyl; R$^3$ and R$^4$ being the same or different and being hydrogen, a lower alkyl of 1 to 7 carbon atoms, an aralkyl compound selected from the group consisting of benzyl, benzyhydryl or methoxybenzyl, or an aryl compound selected from the group consisting of phenyl, chlorophenyl, toluyl, methoxyphenyl and naphthyl; and NHacyl being alkanoyl or aroyl amide, alkanoyl being an alkyl carbonyl radical in which alkyl is a straight or branched chain saturated or unsaturated hydrocarbon radical having from 1 to 20 carbon atoms; and wherein R$^1$ and R$^2$ are the same or different and are acyl or aroyl, acyl being an alkanoyl group of 1 to 20 carbon atoms and aroyl being benzoyl or naphthoyl.

2. A purine nucleoside compound of claim 1 selected from the group consisting of:
 9-(3'-O-acetyl-5'-O-benzoyl-2'-deoxy-2'-fluoro-β-D-arabinofuranosyl)-6-benzamidopurine,
 9-(3'-O-acetyl-5'-O-benzoyl-2'-deoxy-2'-fluoro-β-D-arabinofuranosyl)-6-acetamidopurine,
 9-(3'-O-acetyl-5'-O-benzoyl-2'-deoxy-2'-fluoro-β-D-arabinofuranosyl)-6-acetamido-2-chloropurine,
 9-(3'-O-acetyl-5'-O-benzoyl-2'-deoxy-2'-fluoro-β-D-arabinofuranosyl)-6-benzamido-2-chloropurine,
 9-(3'-O-acetyl-5'-O-benzoyl-2'-deoxy-2'-fluoro-β-D-arabinofuranosyl)-6-acetamido-2-bromopurine,
 9-(3'-O-acetyl-5'-O-benzoyl-2'-deoxy-2'-fluoro-β-D-arabinofuranosyl)-6-benzamido-2-bromopurine,
 9-(3'-O-acetyl-5'-O-benzoyl-2'-deoxy-2'-fluoro-β-D-arabinofuranosyl)-2-acetamidopurine,
 9-(3'-O-acetyl-5'-O-benzoyl-2'-deoxy-2'-fluoro-β-D-arabinofuranosyl)-2-acetamido-6-chloropurine,
 9-(3'-O-acetyl-5'-O-benzoyl-2'-deoxy-2'-fluoro-β-D-arabinofuranosyl)-2-acetamido-6-bromopurine,
 9-(3'-O-acetyl-5'-O-benzoyl-2'-deoxy-2'-fluoro-β-D-arabinofuranosyl)-2-acetamido-6-thiopurine,
 9-(3'-O-acetyl-5-O-benzoyl-2'-deoxy-2'-fluoro-β-D-arabinofuranosyl)-2-benzamidopurine,
 9-(3'-O-acetyl-5'-O-benzoyl-2'-deoxy-2'-fluoro-β-D-arabinofuranosyl)-2-benzamido-6-chloropurine,
 9-(3'-O-acetyl-5'-O-benzoyl-2'-deoxy-2'-fluoro-β-D-arabinofuranosyl)-2-benzamido-6-thiopurine,
 9-(3'-O-acetyl-5'-O-benzoyl-2'-deoxy-2'-fluoro-β-D-arabinofuranosyl)-6-chloropurine,
 9-(3'-O-acetyl-5'-O-benzoyl-2'-deoxy-2'-fluoro-β-D-arabinofuranosyl)-6-bromopurine, and
 9-(3'-O-acetyl-5'-O-benzoyl-2'-deoxy-2'-fluoro-β-D-arabinofuranosyl)-2-methoxy-6-thiopurine.

3. A purine nucleoside compound selected from the group consisting of:
 9-(2'-deoxy-2'-fluoro-β-D-arabinofuranosyl)-hypoxanthine,
 9-(2'-deoxy-2'-fluoro-β-D-arabinofuranosyl)-2-chlorohypoxanthine,
 9-(2'-deoxy-2'-fluoro-β-D-arabinofuranosyl)-2-methoxyhypoxanthine, and
 9-(2'-deoxy-2'-fluoro-β-D-arabinofuranosyl)-2-methylthiohypoxanthine.

4. A pharmaceutical composition comprising an amount of the nucleoside compound of claim 1 or a pharmaceutically acceptable acid addition salt thereof effective to reduce the growth of tumor cells or the growth of *Leishmania tropica* and a pharmaceutically acceptable carrier.

5. A pharmaceutical composition comprising an amount of the nucleoside compound of claim 3 or a pharmaceutically acceptable acid addition salt thereof effective to reduce the growth of tumor cells or the growth of *Leishmania tropica* and a pharmaceutically acceptable carrier.

6. A pharmaceutical composition of claim 5, wherein the nucleoside compound is 9-(2'-deoxy-2'-fluoro-β-D-arabinofuranosyl)hypoxanthine.

* * * * *